United States Patent
Novak

(10) Patent No.: US 7,844,657 B2
(45) Date of Patent: Nov. 30, 2010

(54) SYSTEM FOR CONTROLLING MEDICAL DEVICES

(75) Inventor: Pavel Novak, Stetten (CH)

(73) Assignee: Storz Endoskop Produktions GmbH (DE)

( * ) Notice: Subject to any disclaimer, the term of this patent is extended or adjusted under 35 U.S.C. 154(b) by 1717 days.

(21) Appl. No.: 10/601,406

(22) Filed: Jun. 23, 2003

(65) Prior Publication Data

US 2004/0143677 A1    Jul. 22, 2004

Related U.S. Application Data

(63) Continuation-in-part of application No. 10/346,734, filed on Jan. 17, 2003, now abandoned.

(51) Int. Cl.
*G06F 15/16* (2006.01)

(52) U.S. Cl. .................................. 709/200; 600/109

(58) Field of Classification Search .............. 709/200; 600/109
See application file for complete search history.

(56) References Cited

U.S. PATENT DOCUMENTS

| | | | | |
|---|---|---|---|---|
| 4,519,391 | A | | 5/1985 | Murakoshi .............. 128/303.15 |
| 5,099,846 | A | * | 3/1992 | Hardy ...................... 600/407 |
| 5,217,003 | A | | 6/1993 | Wilk ............................ 128/4 |
| 5,217,453 | A | | 6/1993 | Wilk ............................ 606/7 |
| 5,249,121 | A | | 9/1993 | Baum et al. ............ 364/433.01 |
| 5,500,854 | A | | 3/1996 | Uotila ......................... 370/17 |
| 5,788,688 | A | * | 8/1998 | Bauer et al. ................... 606/1 |
| 5,819,229 | A | * | 10/1998 | Boppe .......................... 705/2 |
| 5,910,139 | A | | 6/1999 | Cochran et al. ............... 606/1 |
| 5,997,528 | A | * | 12/1999 | Bisch et al. ................... 606/1 |
| 6,067,571 | A | * | 5/2000 | Igarashi et al. ............ 709/232 |
| 6,086,576 | A | | 7/2000 | Bisch .......................... 606/1 |
| 6,117,126 | A | | 9/2000 | Appelbaum et al. ............ 606/1 |
| 6,117,127 | A | * | 9/2000 | Helmreich et al. ............. 606/1 |
| 6,397,286 | B1 | | 5/2002 | Chatenever et al. ......... 710/302 |
| 6,459,926 | B1 | | 10/2002 | Nowlin et al. ............... 600/429 |
| 6,480,762 | B1 | | 11/2002 | Uchikubo et al. ........... 700/253 |

(Continued)

FOREIGN PATENT DOCUMENTS

EP    1 068 837 A1    7/2000

(Continued)

OTHER PUBLICATIONS

Irion K M et al. "System Workplace for Endoscopic Surgery" Minimally Invasive Therapy and Allied Technologies 2000 United Kingdom vol. 9, No. 3-4, 2000, pp. 193-197.

(Continued)

*Primary Examiner*—Thu Nguyen
*Assistant Examiner*—Thomas J Dailey
(74) *Attorney, Agent, or Firm*—St. Onge Steward Johnston & Reens LLC

(57) ABSTRACT

A system for controlling medical devices is disclosed, generally comprising a surgical network, an input device for entering a medical command, a controller for generating medical command data, and a translator for communicating with at least one ancillary device, where the ancillary device is either a device that is not compatible with the surgical network or is a device that generates high-bandwidth data. In some embodiments, the ancillary device is connected via Ethernet for high-bandwidth data transmission or via Bluetooth for wireless control.

78 Claims, 3 Drawing Sheets

U.S. PATENT DOCUMENTS

| | | | |
|---|---|---|---|
| 6,490,490 B1 | 12/2002 | Uchikubo et al. | 700/65 |
| 6,496,099 B2 * | 12/2002 | Wang et al. | 340/3.7 |
| 6,581,117 B1 | 6/2003 | Klein et al. | 710/110 |
| 6,589,170 B1 * | 7/2003 | Flach et al. | 600/300 |
| 6,602,185 B1 | 8/2003 | Uchilubo | 600/118 |
| 6,679,875 B2 * | 1/2004 | Honda et al. | 606/1 |
| 6,928,490 B1 * | 8/2005 | Bucholz et al. | 709/249 |
| 7,103,646 B1 * | 9/2006 | Suzuki | 709/220 |
| 2002/0133061 A1 | 9/2002 | Manetta | 600/300 |
| 2002/0147390 A1 | 10/2002 | Markis et al. | 600/301 |
| 2004/0158193 A1 * | 8/2004 | Bui et al. | 604/65 |

FOREIGN PATENT DOCUMENTS

| | | |
|---|---|---|
| EP | 1 198 103 A2 | 9/2001 |
| EP | 1 172064 A2 | 1/2002 |
| WO | WO 00/72180 | 5/2000 |
| WO | WO 00/72180 A2 | 11/2000 |

OTHER PUBLICATIONS

Matias S: "Gateway Fuer Can Der Twincan-Chip Schlaegt Eine Bruecke Zwischen Zwei Voneinander Unabhaengigen Can-Bussystemn" Elektronik, Weka Fachzeitscr. -Verlag, Munchen, DE, vol. 51, No. 5, Mar. 5, 2002 pp. 72-75.

* cited by examiner

SYSTEM FOR CONTROLLING MEDICAL DEVICES

RELATED APPLICATIONS

This is a continuation-in-part of currently pending U.S. patent application Ser. No. 10/346,734, filed Jan. 17, 2003 now abandoned.

FIELD OF THE INVENTION

The invention relates to a system of controlling medical devices in an operating room. Specifically, the invention relates to a system for simultaneously controlling primary medical devices, which are connected to a surgical network, and ancillary devices, which are either not compatible with the surgical network or transmit high-bandwidth data.

BACKGROUND OF THE INVENTION

With the advent of new technologies and continual improvements, the use of medical devices in the operating room has increasingly become more technically complex and increasingly requires more precise operation by the surgeons using the devices. Therefore, various systems for centrally controlling a plurality of medical devices in an operating room have been suggested.

It is generally known to use a central unit to control various medical devices, which can include anything from insufflators, pumps, pressure gauges, lasers, HF instruments, endoscopic lights and cameras, x-ray or ultrasound machines, other image or video recording machines, other illuminating devices, or even a printer, a pager, a telephone, or the operating table itself. One such system uses a self-configuring bus capable of interconnecting a large number of devices to the central unit as a way to centrally control various medical devices in an operating room with a single device. These surgical networks, such as that disclosed in U.S. Pat. No. 6,397,286, which is assigned to the assignee of the present application and which is incorporated herein by reference, may include, for example, a CAN bus monitored by a controller or master device and automatically configured thereby when a particular device connected to the bus is removed from the network, added to the network, or loses power. Such buses permit individual devices to be added or removed from the network without interfering with the operation of the other devices. Additionally, these buses allow a greater number of devices to be used during an individual surgical procedure.

However, one disadvantage of such systems is that the bus does not transmit data as quickly as is sometimes required. The primary purpose of such a bus is to control the devices that the bus interconnects, not the transmission of data generally. Therefore, systems employing CAN or similar buses do not efficiently facilitate the transmission of large amounts of data. However, surgical networks of the kind described above often employ devices that require rapid transmission of large amounts of data, such as, for example, a video camera, which transmits video data back to the central unit and/or a monitor. This data, which can be reproduced as a video image, and can thereby be used to assist with the control of other devices, amounts to a significant amount of information that systems employing CAN or similar buses are not able to efficiently transmit.

Another disadvantage of using a bus such as a CAN or similar bus is that not all of the devices that a surgeon may desire to use during a particular procedure are compatible. As previously noted, there are countless devices that a surgeon may wish to have at his disposal during a particular procedure, and these devices may each be compatible with different bus or network types. Accordingly, it is very likely that a particular surgeon will want to use a medical device that is not compatible with the particular bus or network that is available in his surgical environment.

What is desired, therefore, is a system and method for controlling a plurality of medical devices in which large amounts of data can be transmitted quickly. What is further desired is a system and method for controlling a plurality of medical devices in which certain devices that are not compatible with the first surgical network, or are compatible with a second surgical network, can still be centrally controlled along with the devices of the first surgical network.

SUMMARY OF THE INVENTION

Accordingly, it is an object of the present invention to provide a system for controlling a plurality of medical devices that permits an operator to connect a large number of medical devices to the system.

It is a further object of the present invention to provide a system for controlling a plurality of medical devices that permits the connections of particular devices to be initiated or terminated without interfering with the other devices connected to the system.

It is a further object of the present invention to provide a system for controlling a plurality of medical devices that can communicate large amounts of data quickly.

It is still another object of the present invention to provide a system for controlling a plurality of medical devices that permits the simultaneous control of medical devices that are not compatible with the surgical network.

To overcome the deficiencies in the prior art and achieve at least some of the objects and advantages listed, the invention comprises a system for controlling ancillary medical devices, including a surgical network, an input device, connected to the surgical network, for inputting a medical command, a controller, connected to the surgical network, for receiving the medical command and generating corresponding medical command data, a translator, connected to the surgical network, for receiving and translating the medical command data, at least one ancillary medical device, in communication with the translator, for receiving the translated medical command data and carrying out the corresponding medical command, and a data stream, generated by at least one of the at least one ancillary medical devices and communicated to the translator, with a higher bandwidth than the surgical network is capable of transmitting.

In another embodiment, the invention comprises a system for controlling both primary medical devices, which are part of a surgical network, and ancillary medical devices, including a surgical network, an input device, connected to the surgical network, for inputting a medical command, a controller, connected to the surgical network; for receiving the medical command and generating corresponding medical command data, at least one primary medical device, connected to the surgical network, having a first translator for receiving and translating the medical command data, at least one ancillary medical device, in communication with the first translator, for receiving the translated medical command data and carrying out the corresponding medical command, a data stream, generated by at least one of the at least one ancillary medical devices, with a higher bandwidth than the surgical network is capable of transmitting, and a second translator, in communication with the surgical network, for receiving and translating the data stream.

In yet another embodiment, the invention comprises a system for controlling ancillary medical devices, including, a surgical network, an input device, connected to the surgical network, for inputting a medical command, a controller, connected to the surgical network, for receiving the medical command and generating corresponding medical command data, a translator, connected to the surgical network, for receiving and translating the medical command data, at least one ancillary medical device not connectable to the surgical network, in communication with the translator, for receiving the translated medical command data and carrying out the corresponding medical command, and feedback data generated by the at least one ancillary medical device and communicated to the translator.

In still another embodiment, the invention comprises a system for controlling both primary medical devices, which are part of a surgical network, and ancillary medical devices, including, a surgical network, an input device, connected to the surgical network, for inputting a medical command, a controller, connected to the surgical network, for receiving the medical command and generating corresponding medical command data, at least one primary medical device, connected to the surgical network, having a first translator for receiving and translating the medical command data, at least one ancillary medical device not connectable to the surgical network, connected to the first translator, for receiving the translated medical command data and carrying out the corresponding medical command, feedback data generated by the at least one ancillary medical device, and a second translator, in communication with the surgical network, for receiving and translating the feedback data.

In another embodiment, the invention comprises a system for controlling medical devices, including a surgical network, an input device, connected to the surgical network, for inputting a medical command, a controller, connected to the surgical network, for receiving the medical command and generating corresponding medical command data, an ancillary network, a medical device connected to the surgical network, the device having a first interface, by which the medical device is connected to the surgical network, and a second interface, by which the medical device is in communication with the ancillary network, and a data stream, generated by the medical device and communicated to the ancillary network, with a higher bandwidth than the surgical network is capable of transmitting.

In yet another embodiment, the invention comprises a method for controlling ancillary medical devices, the method including providing a surgical network, entering a medical command into the surgical network, generating corresponding medical command data, translating the medical command data, communicating the translated medical command data to an ancillary medical device, executing the corresponding medical command with the ancillary medical device, generating a data stream, having a higher bandwidth than the surgical network is capable of transmitting, with the ancillary medical device, translating the data stream, and communicating the translated data stream to the surgical network.

In still another embodiment, the invention comprises a method for controlling ancillary medical devices, the method including providing a surgical network, entering a medical command into the surgical network, generating corresponding medical command data, translating the medical command data, communicating the translated medical command data to an ancillary medical device that is not connectable to the surgical network, executing the corresponding medical command with the ancillary medical device, generating feedback data with the ancillary medical device, translating the feedback data, and communicating the translated feedback data to the surgical network.

In another embodiment, the invention comprises a method for controlling medical devices, the method including providing a surgical network, providing an ancillary network, providing a medical device having a first interface and a second interface, entering a medical command into the surgical network, generating corresponding medical command data, communicating the medical command to the medical device via the first interface, executing the medical command with the medical device, generating a data stream, having a higher bandwidth than the surgical network is capable of transmitting, with the medical device, and communicating the data stream to the ancillary network via the second interface.

For this application, the term "not compatible" as used herein means unable to communicate data to, or receive data from, a device or network without the translation of that data.

DETAILED DESCRIPTION OF THE DRAWINGS

Figure 1:
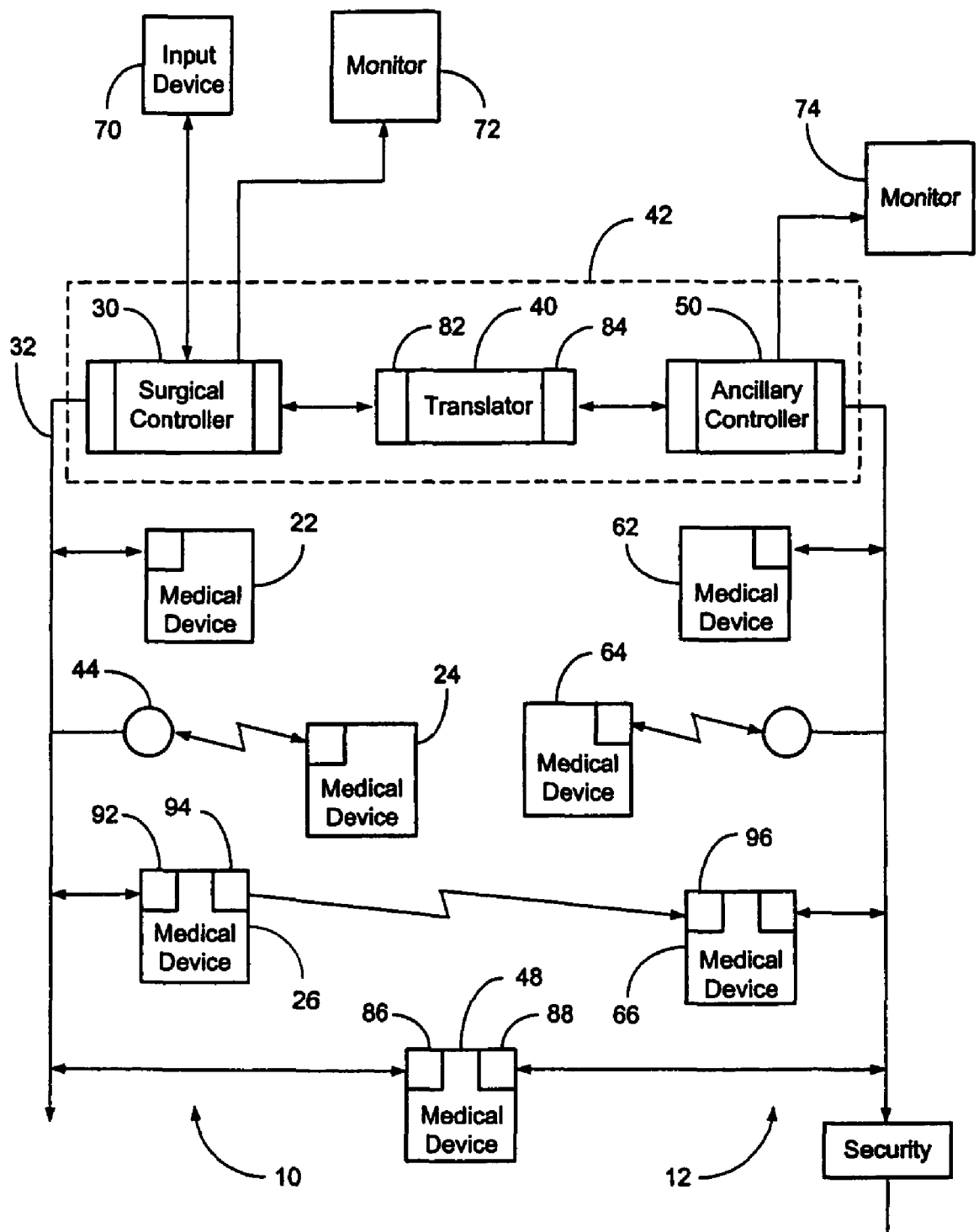
FIG. 1 is a block diagram of a system and method for controlling medical devices in accordance with the invention.

The basic components of one embodiment of a system for controlling medical devices in accordance with the invention are illustrated in FIG. 1. In the embodiment depicted therein, a plurality of devices 22, 24, 26, 48 and a surgical controller 30 are interconnected via a bus 32 to form a surgical network 10. The devices 22, 24, 26, 48 can be any medical devices or related devices that an operator may wish to utilize during a surgical procedure, including, but not limited to, insufflators, pumps, pressure gauges, lasers, HF instruments, endoscopic lights and cameras, x-ray or ultrasound machines, other image or video recording machines, other illuminating devices, or even a printer, a pager, a telephone, or the operating table itself.

In certain advantageous embodiments, the bus 32 is a self-configuring bus, and the surgical controller 30 monitors communication on the bus 32 and is operative to reconfigure the bus 32 when the connections of individual devices 22, 24, 26, 48 to the bus 32 are initiated or terminated. The bus 32 may be any bus capable of being so automatically reconfigured, such as, for example, a Controller Area Network (CAN) bus (i.e. a two-wire serial bus system), or any other bus system with an open architecture and a high level of data integrity.

In some embodiments, a device 22 is connected to the bus 32 via a physical connection. In other embodiments, a transceiver 44 may be physically connected to the bus 32, which transceiver wirelessly connects a device 24 to the bus 32. In certain advantageous embodiments, this connection is a Bluetooth connection.

Typically, the surgical controller 30 is connected to, or includes, a translator 40 having a plurality of interfaces 82, 84 in order to communicate with both the network 10 and at least one other device. However, in some embodiments, the surgical controller 30 does not directly connect to or include a separate translator 40, such as when a device 48 includes a plurality of interfaces 86, 88, as is further explained below.

In some embodiments, the surgical controller 30 is actually one of the devices 22, 24, 26, 48. Such an arrangement may occur when the devices 22, 24, 26, 48 are arranged as a series of master and slave devices. Instead of a separate, non-medical device acting as the surgical controller 30, one of the devices 22, 24, 26, 48 acts as the controller. This master device, such as, for example, device 22, may be any device capable of controlling the slave devices 24, 26, 48. In certain advantageous embodiments, at least some of the slave devices 24, 26, 48 have predetermined priority levels. In these embodiments, if the connection of the master device 22 is terminated or interrupted, whichever of the slave devices 24, 26, 48 has an active connection to the bus 32 and has the highest priority level of all such actively connected devices becomes the new master device, or controller, which then controls the remaining slave devices.

As noted above, the translator 40 has an interface 82 for communicating with the bus 32 and an interface 84 for communicating with at least one other device. Typically, the translator 40 is connected, via the interface 84, to an ancillary controller 50, which is interconnected with a plurality of medical devices 62, 64, 66, 48 to form an ancillary network 12. Similar to the devices 22, 24, 26, 48, the devices 62, 64, 66, 48 can be any medical devices or related devices that an operator may wish to utilize during a surgical procedure, including, but not limited to, insufflators, pumps, pressure gauges, lasers, HF instruments, endoscopic lights and cameras, x-ray or ultrasound machines, other image or video recording machines, other illuminating devices, or even a printer, a pager, a telephone, or the operating table itself.

In certain advantageous embodiments, the connection between the translator 40 and the ancillary network 12 is of the type for which medical devices, or controllers therefor, commonly have an interface. As a result, medical devices that are not compatible with the surgical network 10 can still communicate therewith by receiving data from, or transmitting data to, the translator 40, which translates the data so that the surgical controller 30 and the ancillary controller 50, respectively, can understand the data received therefrom.

In other advantageous embodiments, the connection between the translator 40 and the ancillary network 12 may be any type of connection that is capable of quickly communicating large amounts of data. Though this connection may be one that is able to communicate any high-bandwidth data, in certain advantageous embodiments, it should be able to communicate data at a rate sufficient to support a live video feed from, or real-time visual representation of, the devices of the surgical network 10 and/or ancillary network 12.

In certain advantageous embodiments, this connection is an Ethernet connection. The Ethernet protocol, otherwise known as the IEEE 802.3 standard, facilitates the communication of data via one of various means, such as coaxial cable, twisted pair cable, or fiber-optic cable. Thus, such a connection is able to efficiently communicate high-bandwidth data, such as video data, to the translator 40.

When using an Ethernet connection, point-to-point communication is required. Therefore, in embodiments where there is more than one ancillary device and the connection to the translator 40 is an Ethernet connection, a central device is required to act as a hub or switch. In this way, the ancillary controller 50 permits point-to-point communication between the translator 40 and each of the devices 62, 64, 66, 48.

In other embodiments, this connection is a wireless connection that employs a Bluetooth protocol. Such connections enable a device to communicate data wirelessly to another device, typically within a thirty-five foot range, and have the advantage of not needing a line-of-sight connection.

The interfaces 82, 84 of the translator 40 include devices capable of receiving and directing messages as appropriate between the networks 10 and 12. As a result, the medical devices of the networks 10, 12 are able to send and receive messages to and from the translator 40, which, after translating these messages, will forward appropriate information to the other of the two networks, or to a separate or peripheral device, such as a monitor 72, as is further explained below. In this way, the translator 40 connects the surgical network 10 to the ancillary network 12, allowing the translator 40 to act as a gateway between the two networks, thereby permitting the devices of either network to appear as though they are in the other network. This arrangement (i.e. transparency) permits an operator to control both networks simultaneously and maintains the advantages of a self-configuring bus for both networks. For example, an operator is able to select parameters for display of units in one network within a video image produced by the video data gathered by, and communicated from, a video camera in the other network.

An input device 70 is connected to the surgical controller 30, with which an operator controls the devices of the surgical network 10 and ancillary network 12. The input device 70 can be any device by which an operator can send commands to the devices of networks 10, 12, including, but not limited to, a keyboard, a keypad, a mouse, a trackball, a joystick, a touch screen, or voice recognition software. In some embodiments, the input device 70 is an integral part of, or a peripheral of, the surgical controller 30. In other embodiments, the input device 70 is otherwise connected to the surgical controller 30, either physically or wirelessly. In certain embodiments, the input device 70 is directly or locally connected to the surgical controller 30, while in other embodiments, the input device 70 is remotely connected the surgical controller 30, including, for example, via a network, such that an operator can control the devices remotely, such as, for example, from a separate control room via a Local Area Network, or, for example, from a distant location via the Internet.

In one advantageous embodiment, the surgical controller 30 is a personal computer. Moreover, in certain advantageous embodiments, some or all of the surgical controller 30, translator 40, and ancillary controller 50 are contained within a single device 42, while in other embodiments, they are all separate devices.

In one advantageous embodiment, a video camera 62, which gathers video data during a surgical procedure, is connected to the ancillary controller 50 in order to efficiently communicate the gathered video data to the translator 40, which translates the data and transmits it to the surgical controller 30. It should be noted, however, that any device that the surgeon may desire to use during a surgical procedure may be connected to the ancillary controller 50, particularly any devices that must communicate large amounts of data to the surgical controller 30. In certain advantageous embodiments, the camera 62 is connected to the ancillary controller 50 via an Ethernet connection.

In another advantageous embodiment, a video camera 64 is connected to the ancillary controller 50 via a wireless connection in order to permit less restricted movement of the camera. It should be noted, however, that any device that the surgeon may desire to control wirelessly during a surgical procedure may be connected to the ancillary controller 50 in this way. In certain advantageous embodiments, the connection employs a Bluetooth protocol.

In one advantageous embodiment, a monitor 72 is connected to the surgical controller 30 for reproducing data received by the surgical controller 30 as an image, such as a live video feed or realistic device visualization. In some embodiments, the monitor 72 is an integral part of, or a peripheral of, the surgical controller 30. In other embodiments, the monitor 72 is otherwise connected to the surgical controller 30, either physically or wirelessly. In certain embodiments, the monitor 72 is directly or locally connected to the surgical controller 30, while in other embodiments, the monitor 72 is remotely connected to the surgical controller 30, including, for example, via a network, such that an operator can view the image remotely, such as, for example, in a separate room from which the operator is also operating the input device 70 or, for example, to view the image from a distant location via the Internet. In other embodiments, however, the data may be communicated directly from the device 62, 64, 66, 48 or controller 50 to a monitor 74.

In one embodiment, point-to-point communication between the surgical network 10 is established with ancillary medical device 66 via a wireless connection. In these embodiments, a device 26 connected to the surgical network 10 acts as remote controller for the device 66. The device 26 has its own translator that, after receiving a medical command via the interface 92, translates the data. The translated data is then communicated wirelessly to the device 66 via interfaces 94, 96. Accordingly, if device 66 is not a device that must transmit data, such as, for example, a light, the need for a connection to an ancillary controller 50 is thereby obviated. In certain advantageous embodiments, this connection employs a Bluetooth protocol.

In some embodiments, the ancillary network is, or is connected to, the Internet. In certain embodiments, the single device 42 itself has an interface for connecting directly to the Internet. In this way, data, such as video data, can be transmitted over the Internet, or medical commands can be received therefrom. Similarly, in some embodiments, when the ancillary network 12 is connected to the Internet or some other network, such as a Local Area Network, such as, for example, a hospital information system, separate databases and or processing units may be accessed in order to retrieve data, such as, for example, patient information, or in order to store data, such as, for example, certain video images. Typically, such connections to the Internet employ a security measure, such as, for example, a firewall, electrical isolation, or other security means.

In certain embodiments, the device 48 may have both a bus interface 86 and an Ethernet interface 88. Accordingly, the device 48 can be directly connected to the Internet or the ancillary network 12. In this way, the device 48 may be simultaneously controllable from an additional location besides the input device 70. Further, as a result of this arrangement, the device 48 may be able to receive commands via the interface 86 and transmit high-bandwidth data via the interface 88, and thus, no additional translator is required.

Figure 2:
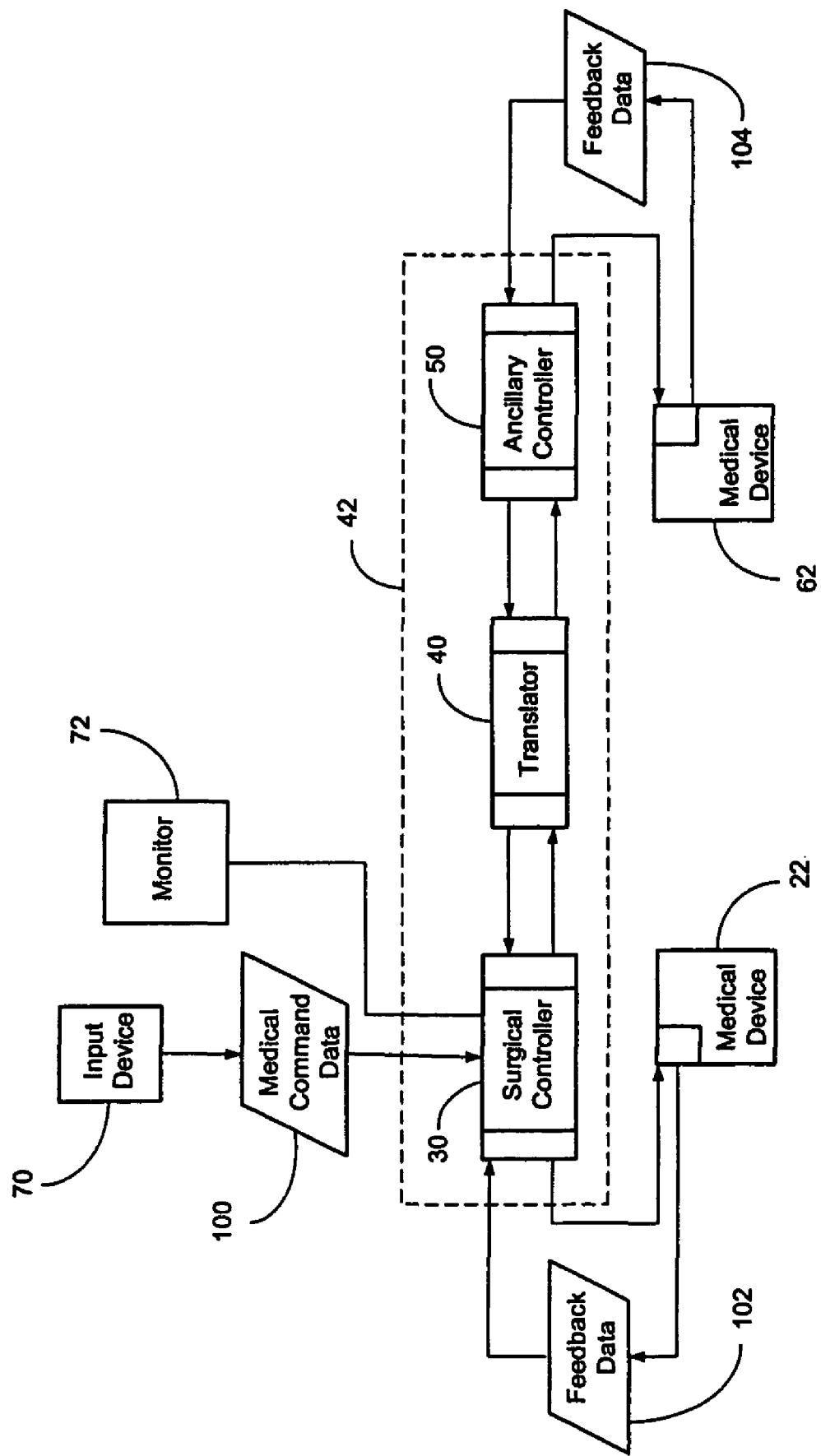
FIG. 2 is a block diagram of one specific embodiment of the system and method of FIG. 1.
Figure 3:
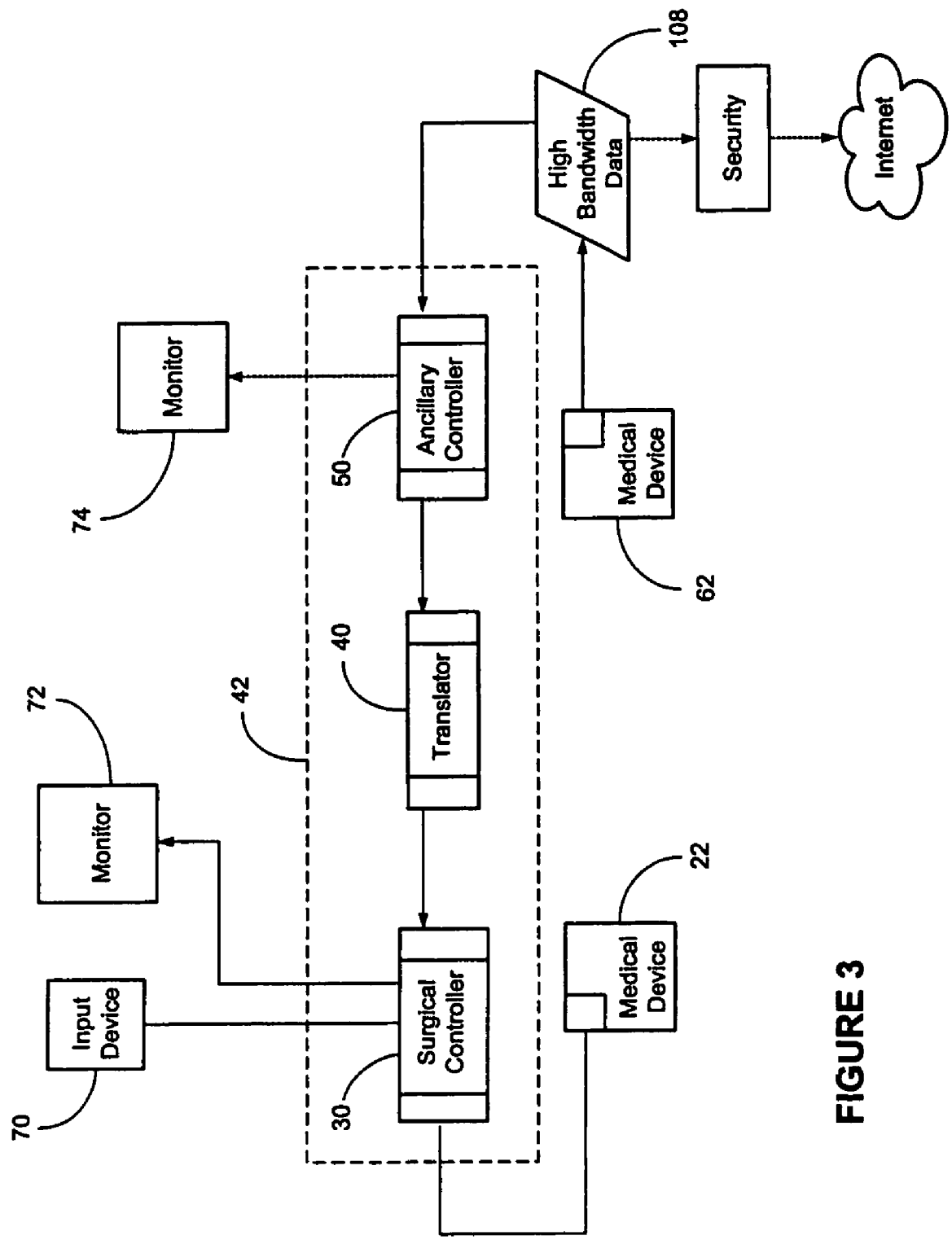
FIG. 3 is a block diagram of a specific embodiment of the system and method of FIG. 2.

Operation of the above described system 10 is illustrated stepwise in FIGS. 2-3. Beginning with FIG. 2, the operator uses the input device 70 to input a command. In response to this command, the input device 70 generates medical command data 100, which is communicated to the surgical controller 30. The surgical controller 30 communicates this data to medical device 22, which executes the command. The medical device 22 then generates feedback data 102, which it communicates back to the surgical controller 30. In some embodiments, medical command data 100 generated by the input device 70 is also communicated from the surgical controller 30 to the translator 40, which translates the data, such as, for example, by using a two dimensional lookup table, and then, in turn, communicates the translated data to the ancillary controller 50. The ancillary controller 50 communicates the translated command data to the medical device 62, which executes the command. The medical device 62 then generates feedback data 104, which it communicates to the ancillary controller 50. The ancillary controller 50 communicates the feedback data 104 to the translator 40, which translates the feedback data, with, for example, a lookup table, and communicates the translated feedback data to the surgical controller 30.

As illustrated in FIG. 3, in certain embodiments, the medical device 62 generates high-bandwidth data 108, which it communicates to the ancillary controller 50. The ancillary controller communicates this high-bandwidth data 108 to the translator 40, which translates the data 108 and communicates the translated data to the surgical controller 30. In certain embodiments, the data is video data, and the surgical controller 30 communicates this data to the monitor 72, which reproduces the data as a video image. In other embodiments, the high-bandwidth data 108 is communicated from the medical device 62 or ancillary controller 50 directly to a monitor 74. In still other embodiments, the high-bandwidth data 108 is communicated from the medical device 62 to the Internet via a secure connection.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A system which controls ancillary medical devices, comprising:
   a surgical network;
   an input device, connected to said surgical network, which inputs a medical command;
   a controller, connected to said surgical network, which receives the medical command and generates corresponding medical command data;
   a translator, connected to said surgical network, which receives the medical command data via said surgical network and translates the medical command data;
   at least one ancillary medical device, in communication with said translator via an ancillary network, which receives the translated medical command data and carries out the corresponding medical command; and
   a data stream, generated by at least one of said at least one ancillary medical devices and communicated to said translator via said ancillary network, with a higher bandwidth than said surgical network is capable of transmitting.

2. The system of claim 1, wherein said input device is connected to said controller.

3. The system of claim 1, wherein said translator is in communication with at least one of said at least one ancillary medical devices via an Ethernet connection.

4. The system of claim 1, wherein said translator is in communication with at least one of said at least one ancillary medical devices via a wireless connection.

5. The system of claim 4, wherein said wireless connection is a Bluetooth connection.

6. The system of claim 1, wherein said surgical network includes a self-configuring bus.

7. The system of claim 6, wherein said bus is a CAN bus.

8. The system of claim 1, wherein said surgical network comprises an Ethernet.

9. The system of claim 1, further comprising an ancillary controller connected to said ancillary network.

10. The system of claim 9, wherein said ancillary network includes an ancillary input device.

11. The system of claim 10, wherein said ancillary input device is connected to said ancillary controller.

12. The system of claim 9, wherein said translator is in communication with said ancillary controller via an Ethernet connection.

13. The system of claim 9, wherein at least one of said at least one ancillary medical devices is in communication with said ancillary controller via a wireless connection.

14. The system of claim 13, wherein said wireless connection is a Bluetooth connection.

15. The system of claim 1, wherein said ancillary network includes a self-configuring bus.

16. The system of claim 1, wherein said ancillary network comprises an Ethernet.

17. The system of claim 1, wherein said translator includes a lookup table for performing translations.

18. The system of claim 1, wherein said data stream is video data, the system further comprising a monitor, which is connected to said surgical network, which reproduces said video data as a video image after said video data has been translated by said translator.

19. The system of claim 18, wherein the video image is a live video feed.

20. The system of claim 18, wherein said surgical network includes at least one primary medical device, and the video image is a visual representation of at least one of said primary or ancillary medical devices.

21. A system which controls ancillary medical devices, comprising:
   a surgical network;
   an input device, connected to said surgical network, which inputs a medical command;
   a controller, connected to said surgical network, which receives the medical command and generates corresponding medical command data;
   a translator, connected to said surgical network, which receives the medical command data via said surgical network and translates the medical command data;
   at least one ancillary medical device not connectable to said surgical network, in communication with said translator via an ancillary network, which receives the translated medical command data and carries out the corresponding medical command; and
   feedback data generated by said at least one ancillary medical device and communicated to said translator via said ancillary network.

22. The system of claim 21, wherein said input device is connected to said controller.

23. The system of claim 21, wherein said translator is in communication with at least one of said at least one ancillary medical device via an Ethernet connection.

24. The system of claim 21, wherein said translator is in communication with at least one of said at least one ancillary medical devices via a wireless connection.

25. The system of claim 24, wherein said wireless connection is a Bluetooth connection.

26. The system of claim 21, wherein said surgical network includes a self-configuring bus.

27. The system of claim 26, wherein said bus is a CAN bus.

28. The system of claim 21, wherein said surgical network comprises an Ethernet.

29. The system of claim 21, further comprising an ancillary controller connected to said ancillary network.

30. The system of claim 29, wherein said ancillary network includes an ancillary input device.

31. The system of claim 30, wherein said ancillary input device is connected to said ancillary controller.

32. The system of claim 29, wherein said translator is in communication with said ancillary controller via an Ethernet connection.

33. The system of claim 29, wherein at least one of said at least one ancillary medical devices is in communication with said ancillary controller via a wireless connection.

34. The system of claim 33, wherein said wireless connection is a Bluetooth connection.

35. The system of claim 21, wherein said ancillary network includes a self-configuring bus.

36. The system of claim 21, wherein said ancillary network comprises an Ethernet.

37. The system of claim 21, wherein said translator includes a lookup table for performing translations.

38. A system for controlling both primary medical devices, which are part of a surgical network, and ancillary medical devices, comprising:
   a surgical network;
   an input device, connected to said surgical network, which inputs a medical command;
   a controller, connected to said surgical network; which receives the medical command and generates corresponding medical command data;
   at least one primary medical device, connected to said surgical network, having a first translator which receives the medical command data via said surgical network and translates the medical command data;
   at least one ancillary medical device, in communication with the first translator, which receives the translated medical command data and carries out the corresponding medical command;
   a data stream, generated by at least one of said at least one ancillary medical devices, with a higher bandwidth than said surgical network is capable of transmitting; and
   a second translator, in communication both with said surgical network and with an ancillary network, which receives said data stream via said ancillary network and translates said data stream.

39. A system which controls both primary medical devices, which are part of a surgical network, and ancillary medical devices, comprising:
   a surgical network;
   an input device, connected to said surgical network, which inputs a medical command;
   a controller, connected to said surgical network, which receives the medical command and generates corresponding medical command data;
   at least one primary medical device, connected to said surgical network, having a first translator which receives the medical command data via said surgical network and translates the medical command data;
   at least one ancillary medical device not connectable to said surgical network, connected to said first translator, which receives the translated medical command data and carries out the corresponding medical command;
   feedback data generated by said at least one ancillary medical device; and a second translator, in communication both with said surgical network and with an ancillary network, which receives said feedback data via said ancillary network and translates said feedback data.

40. A system which controls medical devices, comprising:
   a surgical network;
   an input device, connected to said surgical network, which inputs a medical command;
   a controller, connected to said surgical network, which receives the medical command and generates corresponding medical command data;

an ancillary network;

a medical device connected to said surgical network, said device having a first interface, by which said medical device is connected to said surgical network and by which said medical device receives the command data via said surgical network, and a second interface, by which said medical device is in communication with said ancillary network; and a data stream, generated by said medical device and communicated to said ancillary network, with a higher bandwidth than said surgical network is capable of transmitting.

41. A method for controlling ancillary medical devices, the method comprising:

providing a surgical network;
entering a medical command into the surgical network;
generating corresponding medical command data;
communicating the medical command data via the surgical network;
translating the medical command data;
communicating the translated medical command data to an ancillary medical device;
executing the corresponding medical command with the ancillary medical device;
generating a data stream, having a higher bandwidth than the surgical network is capable of transmitting, with the ancillary medical device;
communicating the data stream via an ancillary network;
translating the data stream; and communicating the translated data stream to the surgical network.

42. The method of claim 41, wherein the medical command is entered with an input device that is connected to a controller that generates the corresponding medical command data.

43. The method of claim 41, wherein the medical command data is communicated to, and the data stream is communicated from, the ancillary medical device via an Ethernet connection.

44. The method of claim 41, wherein the medical command data is communicated to, and the data stream is communicated from, the ancillary medical device via a wireless connection.

45. The method of claim 44, wherein the wireless connection is a Bluetooth connection.

46. The method of claim 41, wherein the surgical network includes a self-configuring bus.

47. The method of claim 46, wherein the bus is a CAN bus.

48. The method of claim 41, wherein the surgical network comprises an Ethernet.

49. The method of claim 41, wherein an ancillary controller is connected to the ancillary network.

50. The method of claim 49, wherein an ancillary input device is connected to the ancillary network.

51. The method of claim 50, wherein the ancillary input device is connected to the ancillary controller.

52. The method of claim 49, wherein the translator communicates with the ancillary controller via an Ethernet connection.

53. The method of claim 49, wherein the translator communicates with the ancillary controller via a wireless connection.

54. The method of claim 53, wherein the wireless connection is a Bluetooth connection.

55. The method of claim 41, wherein the ancillary network includes a self-configuring bus.

56. The method of claim 41, wherein the ancillary network comprises an Ethernet.

57. The method of claim 41, wherein the medical command data and the data stream are each translated by a lookup table.

58. The method of claim 41, wherein the data stream is video data, further comprising the step of reproducing the video data as a video image.

59. The method of claim 58, wherein the step of reproducing the video data as a video image includes reproducing a live video feed.

60. The method of claim 58, wherein the step of reproducing the video data as a video image includes reproducing a visual representation of the ancillary medical device or another medical device.

61. A method for controlling ancillary medical devices, the method comprising:

providing a surgical network;
entering a medical command into the surgical network;
generating corresponding medical command data;
communicating the medical command data via the surgical network;
translating the medical command data;
communicating the translated medical command data to an ancillary medical device that is not connectable to the surgical network;
executing the corresponding medical command with the ancillary medical device;
generating feedback data with the ancillary medical device;
communicating the feedback data via an ancillary network;
translating the feedback data; and
communicating the translated feedback data to the surgical network.

62. The method of claim 61, wherein the medical command is entered with an input device that is connected to a controller that generates the corresponding medical command data.

63. The method of claim 61, wherein the medical command data is communicated to, and the feedback data is communicated from, the ancillary medical device via an Ethernet connection.

64. The method of claim 61, wherein the medical command data is communicated to, and the feedback data is communicated from, the ancillary medical device via a wireless connection.

65. The method of claim 64, wherein the wireless connection is a Bluetooth connection.

66. The method of claim 61, wherein the surgical network includes a self-configuring bus.

67. The method of claim 66, wherein the bus is a CAN bus.

68. The method of claim 61, wherein the surgical network comprises an Ethernet.

69. The method of claim 61, wherein an ancillary controller is connected to the ancillary network.

70. The method of claim 69, wherein an ancillary input device is connected to the ancillary network.

71. The method of claim 70, wherein the ancillary input device is connected to the ancillary controller.

72. The method of claim 69, wherein the translator communicates with the ancillary controller via an Ethernet connection.

73. The method of claim 69, wherein the translator communicates with the ancillary controller via a wireless connection.

74. The method of claim 73, wherein the wireless connection is a Bluetooth connection.

75. The method of claim 61, wherein the ancillary network includes a self-configuring bus.

76. The method of claim 61, wherein the ancillary network comprises an Ethernet.

77. The method of claim 61, wherein the medical command data and the feedback data are each translated by a lookup table.

78. A method for controlling medical devices, the method comprising:

provatiding a surgical network;

providing an ancillary network;

providing a medical device having a first interface and a second interface;

entering a medical command into the surgical network;

generating corresponding medical command data;

communicating the medical command to the medical device via the first interface via the surgical network;

executing the medical command with the medical device;

generating a data stream, having a higher bandwidth than said surgical network is capable of transmitting, with the medical device; and communicating the data stream to the ancillary network via the second interface.

* * * * *

UNITED STATES PATENT AND TRADEMARK OFFICE
Certificate

Patent No. 7,844,657 B2                                                    Patented: November 30, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Pavel Novak, Stetten (CH); Heinz- Werner Stiller, Beringen (CH); and Tasso Stroehle, Messkirch (DE).

Signed and Sealed this Twenty-fifth Day of March 2014.

*THU NGUYEN*
*Supervisory Patent Examiner*
*Art Unit 2452*
*Technology Center 2400*